US011116461B2

(12) United States Patent
Khamaisi et al.

(10) Patent No.: US 11,116,461 B2
(45) Date of Patent: Sep. 14, 2021

(54) METHOD AND SYSTEM FOR FLUID COOLED VARIABLE SIZE GANTRY BORE

(71) Applicant: GE Precision Healthcare LLC, Wauwatosa, WI (US)

(72) Inventors: Raed Khamaisi, Karmeil (IL); Asaf Shtern, Betset (IL)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 50 days.

(21) Appl. No.: 16/662,244

(22) Filed: Oct. 24, 2019

(65) Prior Publication Data

US 2021/0121144 A1    Apr. 29, 2021

(51) Int. Cl.
*A61B 6/00*    (2006.01)
*A61B 6/03*    (2006.01)
*G01T 1/29*    (2006.01)

(52) U.S. Cl.
CPC ............ *A61B 6/4488* (2013.01); *A61B 6/035* (2013.01); *A61B 6/037* (2013.01); *G01T 1/2985* (2013.01)

(58) Field of Classification Search
CPC ....... A61B 6/4488; A61B 6/037; A61B 6/035; G01T 1/2985
See application file for complete search history.

(56) References Cited

U.S. PATENT DOCUMENTS

| | | | |
|---|---|---|---|
| 6,249,563 B1* | 6/2001 | Snyder | G01N 23/046 378/19 |
| 2006/0065848 A1* | 3/2006 | Ueno | A61B 6/4488 250/370.15 |
| 2013/0119259 A1* | 5/2013 | Martin | G01T 1/1648 250/363.03 |
| 2015/0018673 A1 | 1/2015 | Rose et al. | |
| 2015/0119704 A1 | 4/2015 | Roth et al. | |
| 2018/0000431 A1 | 1/2018 | Roth et al. | |
| 2018/0059270 A1* | 3/2018 | Hefetz | A61B 6/037 |

FOREIGN PATENT DOCUMENTS

| | | |
|---|---|---|
| CN | 102178542 B | 9/2011 |
| WO | 2019077542 A2 | 4/2019 |

\* cited by examiner

*Primary Examiner* — Michael C Bryant
(74) *Attorney, Agent, or Firm* — McAndrews, Held & Malloy, Ltd.; Jacob Groethe; Daniel Guiser (57) ABSTRACT

An imaging system comprises an adaptor plate configured to be removably coupled to a gantry structure of the imaging system, a plurality of detectors configured to be removably coupled to the adaptor plate, and one or more conduits for a fluid to flow through, wherein the fluid is used to cool the imaging system.

20 Claims, 10 Drawing Sheets

METHOD AND SYSTEM FOR FLUID COOLED VARIABLE SIZE GANTRY BORE

FIELD

Certain embodiments relate to a gantry bore. More specifically, certain embodiments relate to a method and system for providing fluid cooled variable size gantry bore.

BACKGROUND

Medical imaging machines may sometimes be used for imaging at least a portion of a patient's body as part of diagnostic procedures. The imaging machines may be, for example, positron emission tomography (PET) scanner, a single photon emission tomography scanner, etc., and hybrid imaging machines of the above technologies. The patient may be placed on a bed, and the bed may be moved into position through a bore of the gantry of the imaging machine so that the imaging machine may make appropriate images of the patient. An imaging machine may be provided with different sized gantries based on the needs of the imaging machine. For example, if the imaging machine is intended for a pediatric hospital, the bore of the imaging machine may be smaller than if the imaging machine is intended for a hospital that caters to all patients, including adults. Depending on the size of the gantry bore, the number of detectors for the PET scanner may change. Accordingly, the cost of the PET scanner may be less for the smaller bore PET scanner.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for providing fluid cooled variable size gantry bore, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for fluid cooled variable size gantry bore.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between mechanical parts and/or hardware circuitry. The fluid used for cooling may be liquid or gas.

It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "imaging machine" broadly refers to a PET scanner, a CAT scanner, an MRI scanner, or any other medical imaging machines that is capable of scanning at least a part of a patient.

Figure 1:
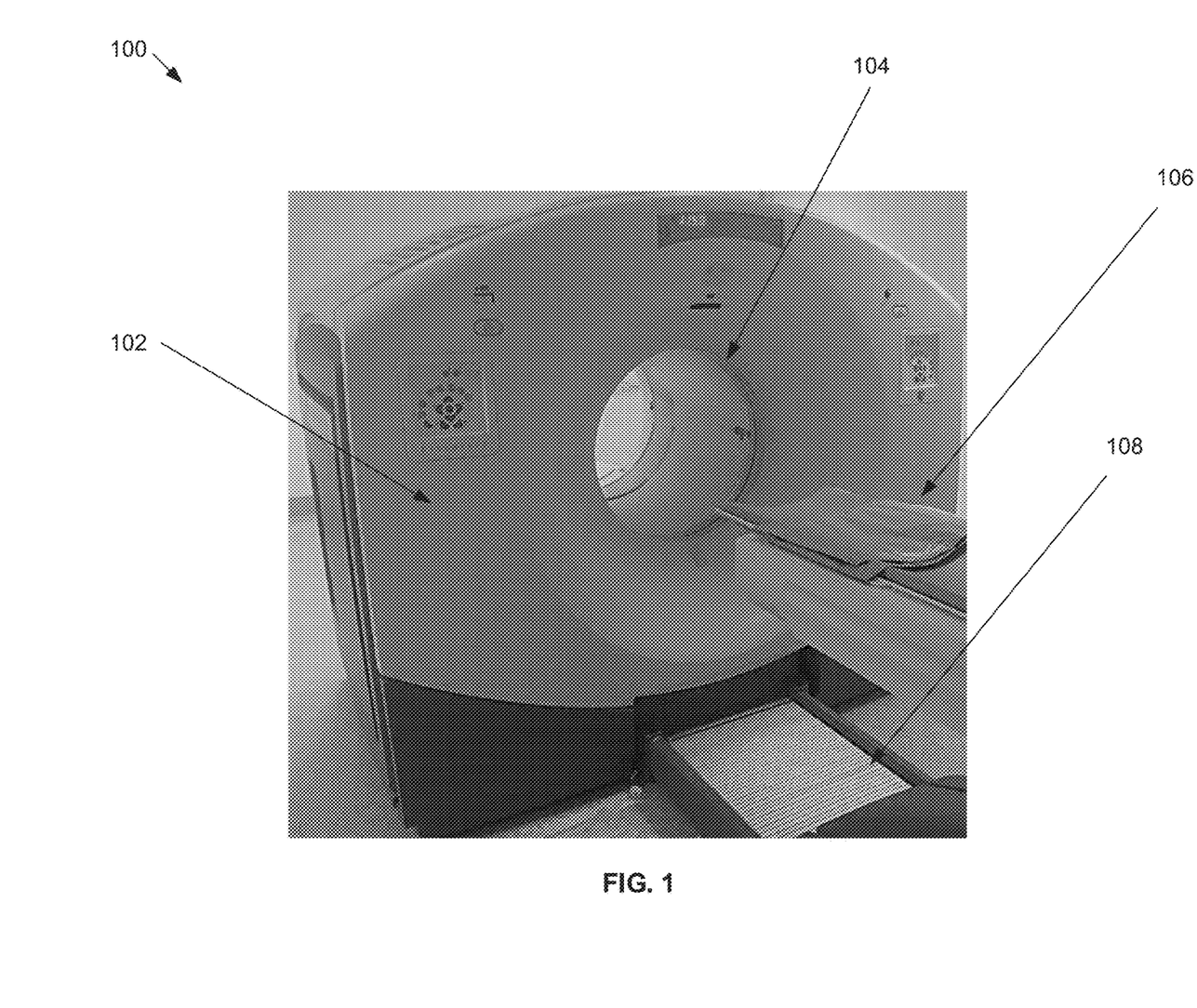
FIG. 1 is a diagram of an example PET scanner, in accordance with various embodiments.

FIG. 1 is a diagram of an example PET scanner, in accordance with various embodiments. Referring to FIG. 1, there is shown a PET scanner 100 comprising a gantry 102, a gantry bore 104, a patient bed 106, a bed base 108. A patient may lie on the patient bed 106, and the patient bed 106 can be moved through the gantry bore 104 into the gantry 102 so that the PET scanner 100 can take images of the patient. The bed base 108, which is attached to the patient bed 106, may move the patient bed in to or out of the gantry 102.

As shown in FIGS. 2A-7B, inside the gantry 102 is a gantry mechanism that may comprise a gantry structure, an adaptor plate removably mounted to the gantry structure, and PET detectors removably mounted to the adaptor plate.

Figure 2A:
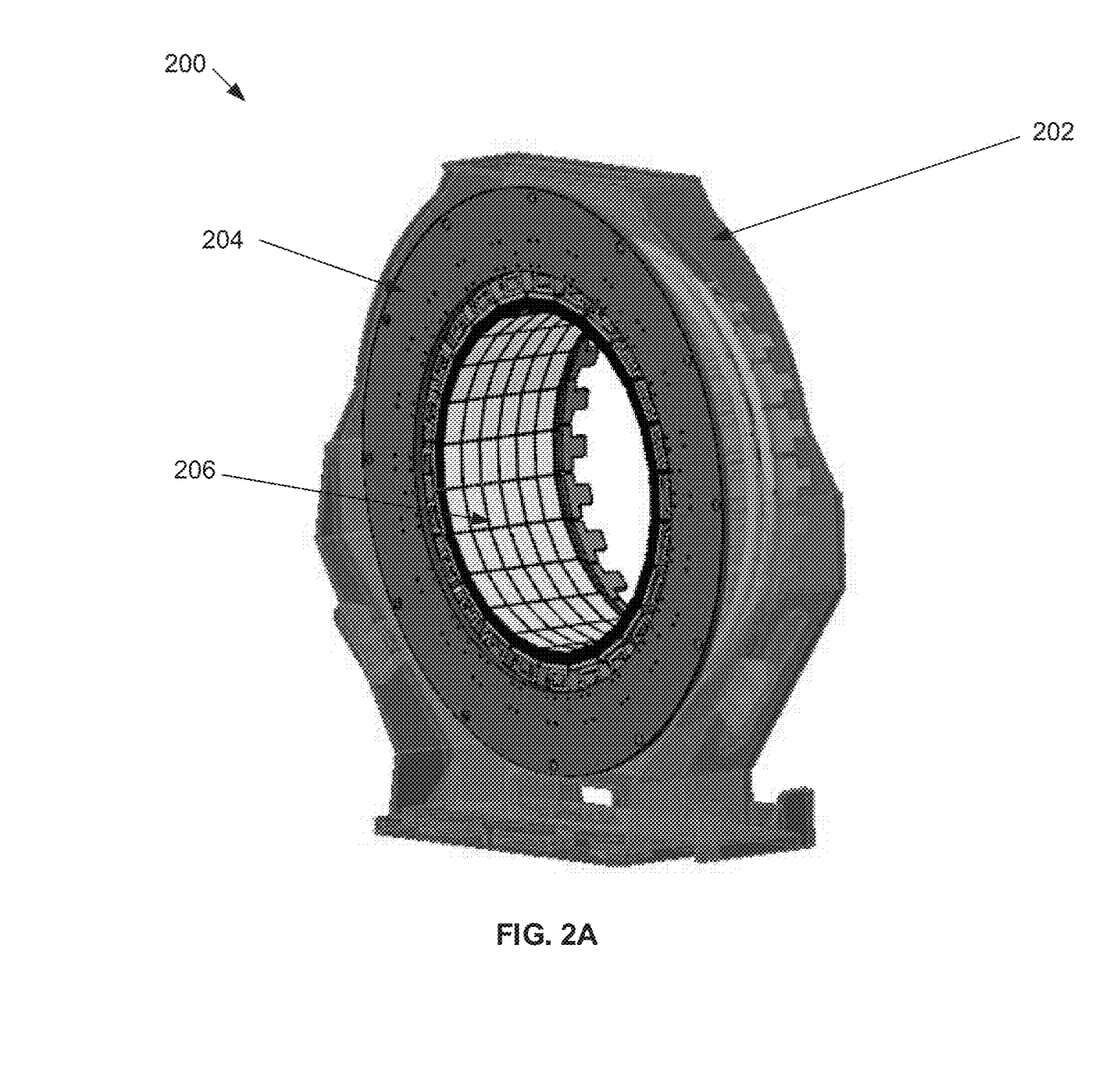
FIG. 2A is a diagram of an example PET scanner gantry structure with detectors, in accordance with various embodiments.

FIG. 2A is a diagram of an example PET scanner gantry structure with detectors, in accordance with various embodiments. Referring to FIG. 2A, there is shown a gantry mechanism 200 comprising the gantry structure 202, the adaptor plate 204, and the PET detectors 206. The gantry mechanism 200 may be used with the PET scanner 100.

There may be multiple adaptor plates 204 to choose from for the gantry mechanism 200, where each adaptor plate 204 may have a different bore (opening) size. An appropriate adaptor plate 204 may be used for specific purposes. For example, when the PET scanner 100 is meant for children, an adaptor plate 204 with a small bore size may be ordered. The PET scanner 100 may also use different adaptor plates 204 in different regions of the world where the size of the adult patients may be different.

When an adaptor plate 204 is selected, the number of PET detectors 206 removably coupled to the adaptor plate 204 may change depending on the bore size of the adapter plate 204. Accordingly, when a PET scanner 100 is ordered, using a smaller adaptor plate 204 may require fewer PET detectors 206 than using a larger adaptor plate 204. Using fewer PET detectors 206 may result in a cheaper price for the finished PET scanner 100.

The adaptor plate 204 may be removably coupled to the gantry structure 202 using, for example, bolts. Accordingly, the adaptor plate 204 may have holes where the bolts can be inserted to thread into, for example, correspondingly threaded holes in the gantry structure 202. In some embodiments, the adaptor plate 204 may also have the bolt holes threaded. Each of the PET detectors 206 may be removably coupled to the adaptor plate 204. For example, each of the PET detectors 206 may be removably coupled to the adaptor plate 204 using, for example, bolts, where the holes in the adaptor plate 204 and/or the corresponding holes in the PET detectors 206 may be threaded.

Various embodiments may have a supports (not shown) on the adaptor plate 204 to align the PET detectors 206. Other embodiments may allow the PET detectors 206 to align with PET detectors 206 on either side. For example, each PET detector 206 may have a notch (not shown) on a first side and a corresponding tab (not shown) on a second side so that the tab of a first PET detector 206 can fit into a notch of a second PET detector 206, etc.

Figure 2B:
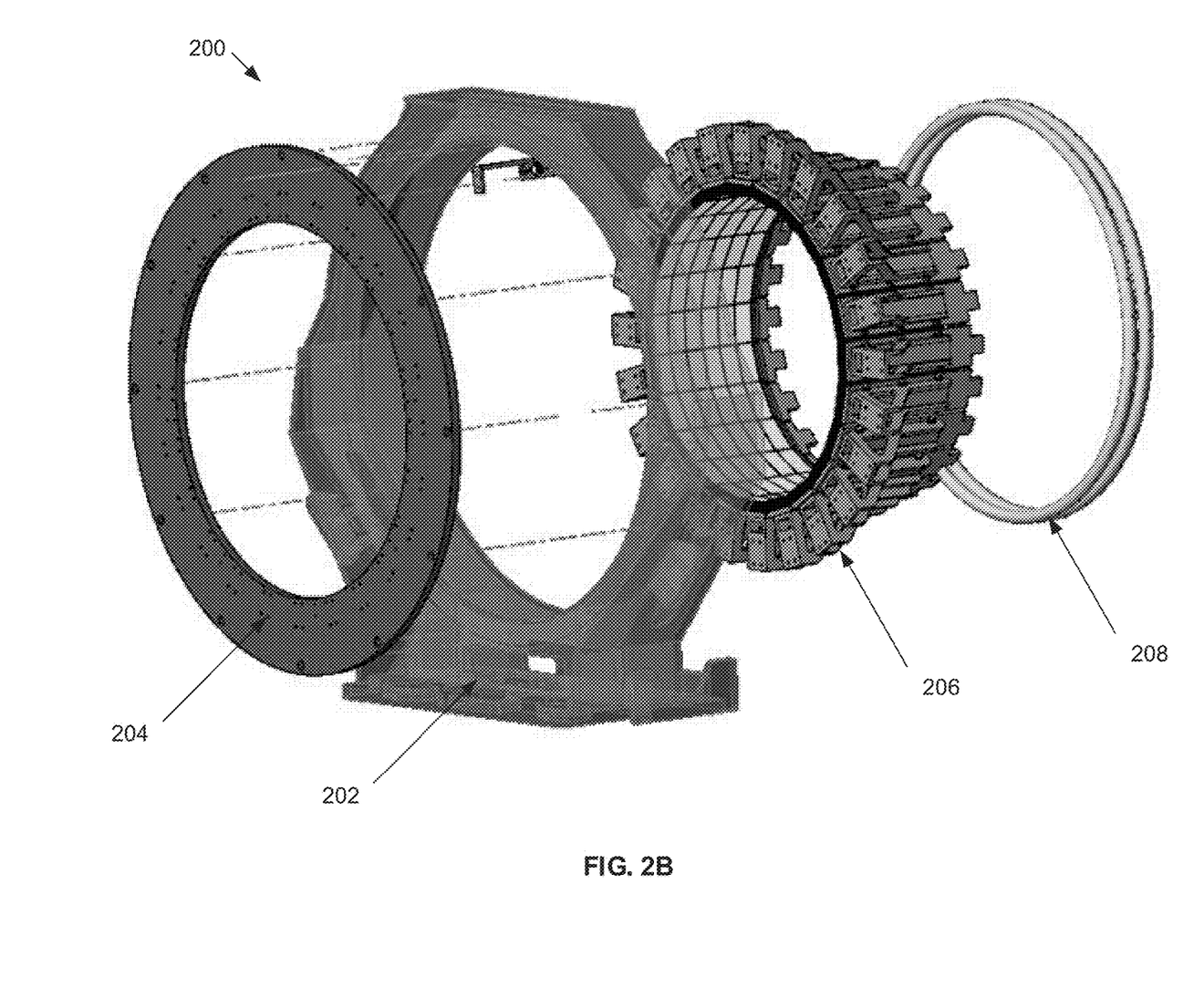
FIG. 2B is an exploded view of the example PET scanner gantry structure with detectors of FIG. 2A, in accordance with various embodiments.

FIG. 2B is an exploded view of the example PET scanner gantry structure with detectors of FIG. 2A, in accordance with various embodiments. Referring to FIG. 2B, there is shown the gantry mechanism 200 comprising the gantry structure 202, the adaptor plate 204, and the PET detectors 206. The gantry mechanism 200 may be used with the PET scanner 100. There is also shown a cooling liquid manifold 208. The cooling liquid manifold may be used in, for example, a liquid-cooled PET scanner gantry structure with detectors. This is described in more detail with respect to FIGS. 7A and 7B.

Figure 3A:
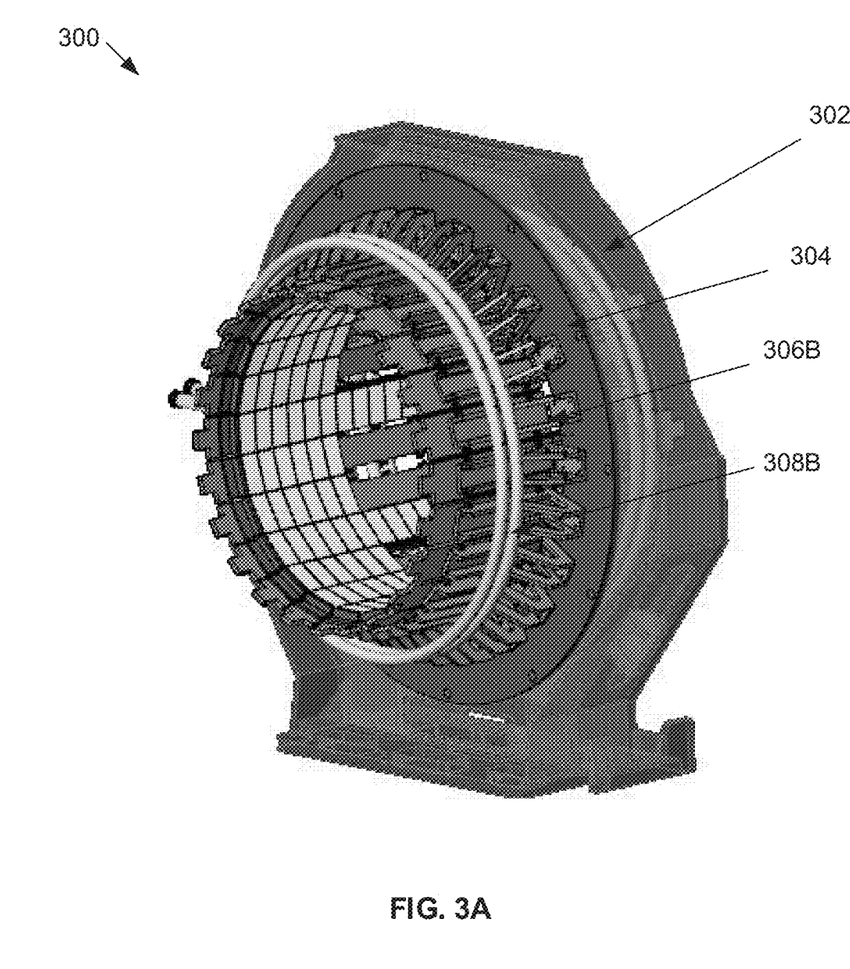
FIG. 3A is a diagram of another example PET scanner gantry structure with detectors, in accordance with various embodiments.

FIG. 3A is a diagram of another example PET scanner gantry structure with detectors, in accordance with various embodiments. The example gantry mechanism 300 may be similar to the gantry mechanism 200, but the gantry mechanism 300 may comprise PET detectors 306B in addition to the PET detectors 206 shown in FIGS. 2A and 2B. Accordingly, there may be PET detectors removably coupled to both sides of the adaptor plate 304 in FIG. 3A. Additionally, there may be a second cooling liquid manifold 208 to cool the second set of PET detectors 306B.

Figure 3B:
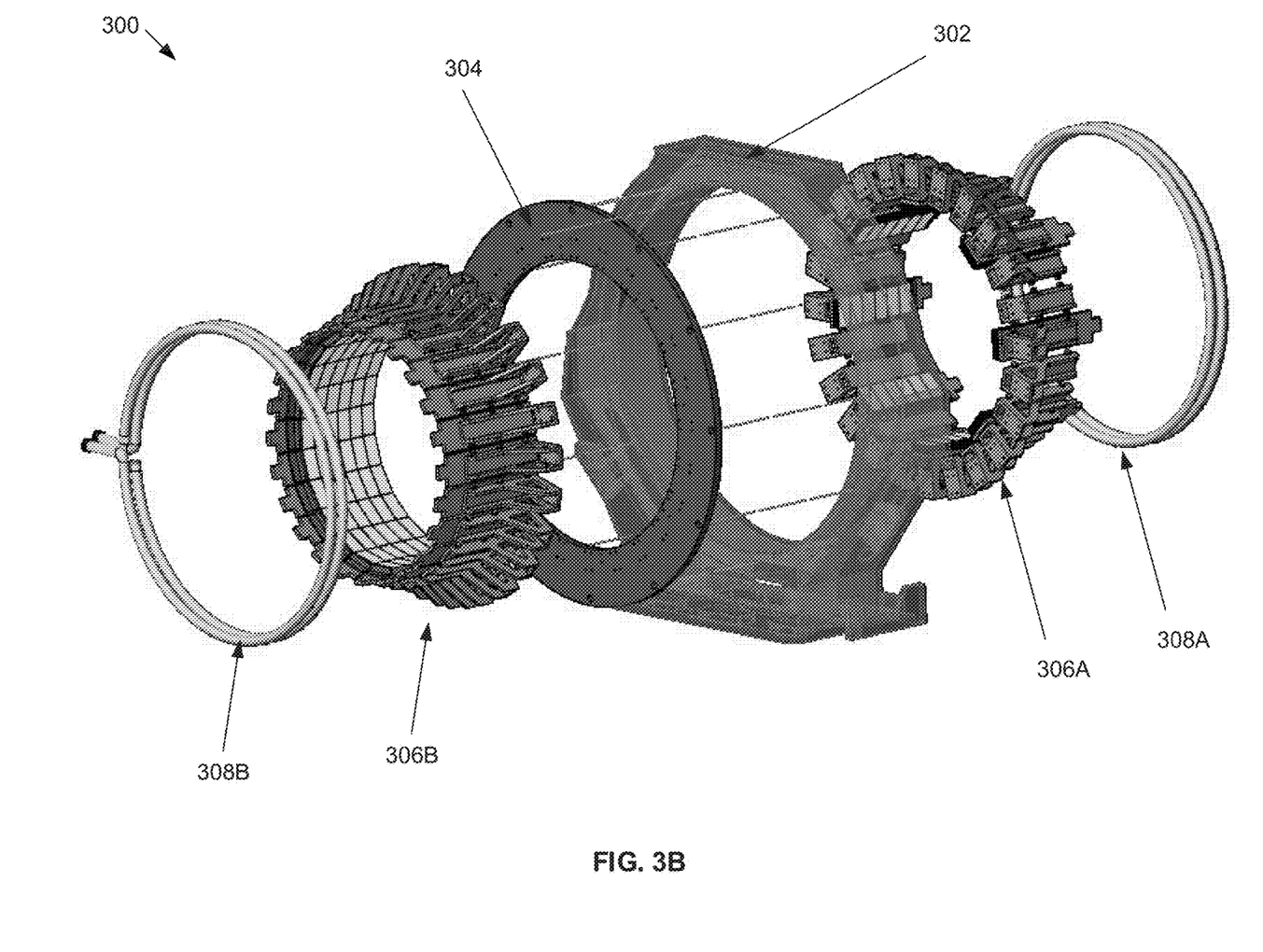
FIG. 3B is an exploded view of the example PET scanner gantry structure with detectors of FIG. 3A, in accordance with various embodiments.

FIG. 3B is an exploded view of the example PET scanner gantry structure with detectors of FIG. 3A, in accordance with various embodiments. Referring to FIG. 3B, there is shown the gantry mechanism 300 comprising a gantry structure 302, an adaptor plate 304, PET detectors 306A and 306B, and cooling liquid manifolds 308A and 308B. The gantry mechanism 300 may be used with the PET scanner 100.

The adaptor plate 304 may be removably coupled to the gantry structure 302 and the PET detectors 306A and 306B may be removably coupled to the gantry structure 302 similarly as described with respect to FIGS. 2A and 2B.

Figure 4:
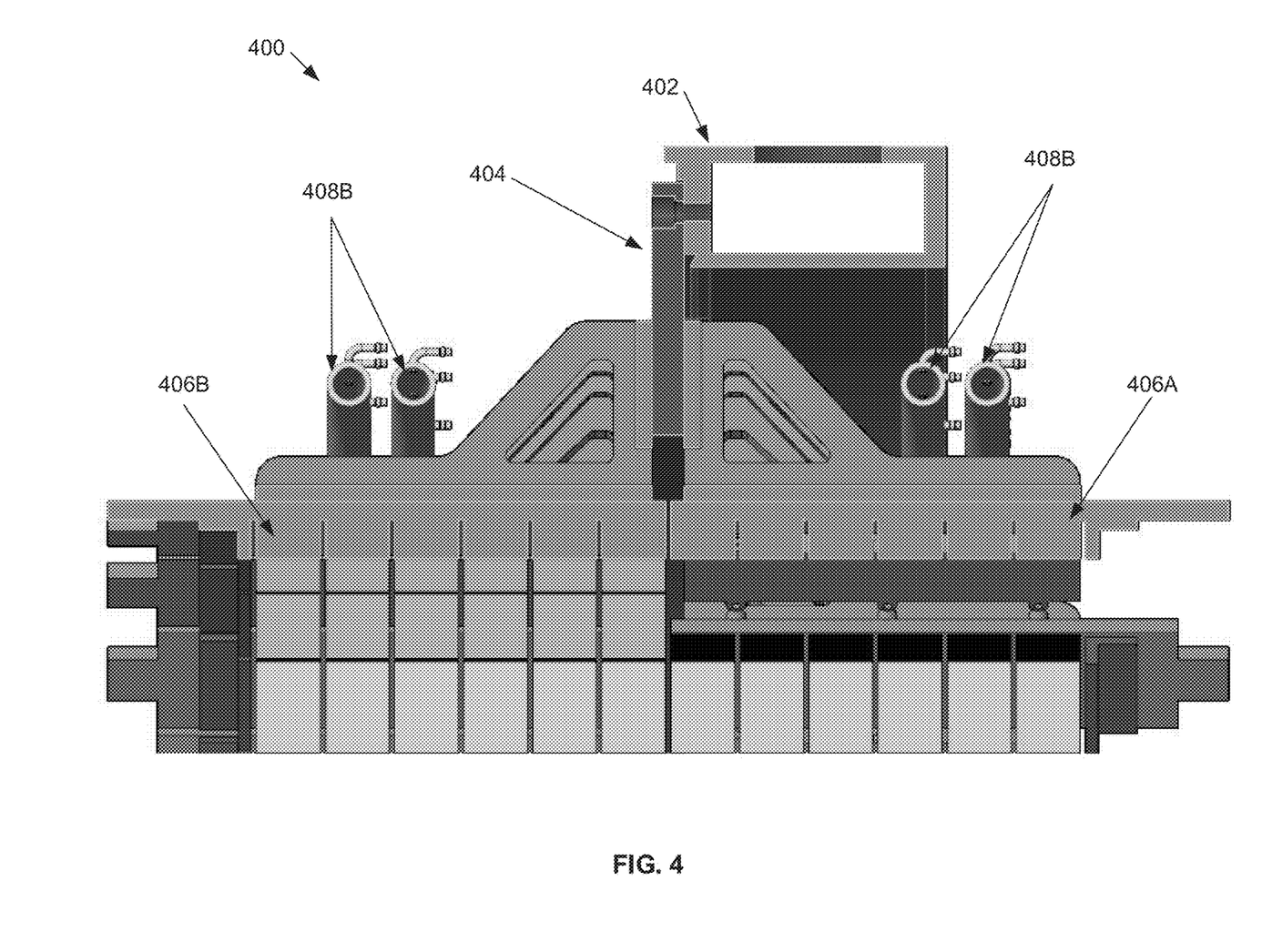
FIG. 4 is a cross-section of a side view of the example PET scanner gantry structure with detectors of FIG. 3A, in accordance with various embodiments.

FIG. 4 is a cross-section of a side view of the example PET scanner gantry structure with detectors of FIG. 3A, in accordance with various embodiments. Referring to FIG. 4, there is shown a gantry mechanism 400 comprising a gantry structure 402, an adaptor plate 404, PET detectors 406A and 406B, and cooling liquid manifolds 408A and 408B.

Figure 5:
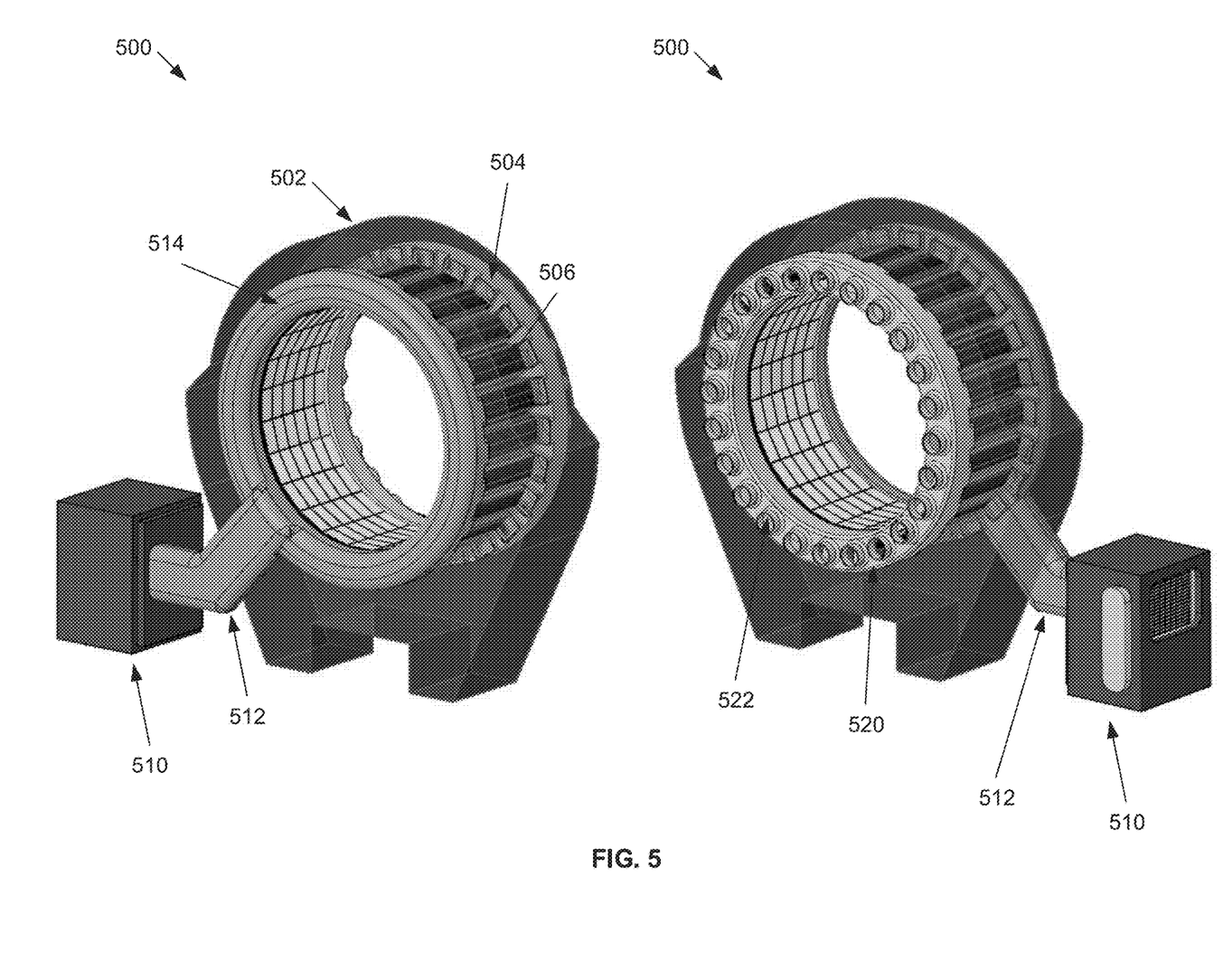
FIG. 5 is a first view of an example air-cooled PET scanner gantry structure with detectors, in accordance with various embodiments.

FIG. 5 is an illustration of an example air-cooled PET scanner gantry structure with detectors, in accordance with various embodiments. Referring to FIG. 5, there is shown a gantry mechanism 500 that is air cooled by a blower 510, where air from the blower 510 may be provided to an air inlet manifold 514 via the air conduit 512. The air provided to the inlet manifold 514 may blow over the PET detectors 506 to cool the PET detectors 506.

The air inlet manifold 514 may be at a first end where the PET detectors 506 are removably coupled to the adaptor plate 504 or at a second end where the PET detectors 506 are not coupled to the adaptor plate 504. The adaptor plate 504 may have holes (not shown) to allow entry of the air to flow over the PET detectors 506, or exit of the air that flowed over the PET detectors 506.

In various embodiments, the blower 510 may be, for example, an air conditioner that cools the air before providing the cooled air to the air inlet manifold 514.

Figure 6:
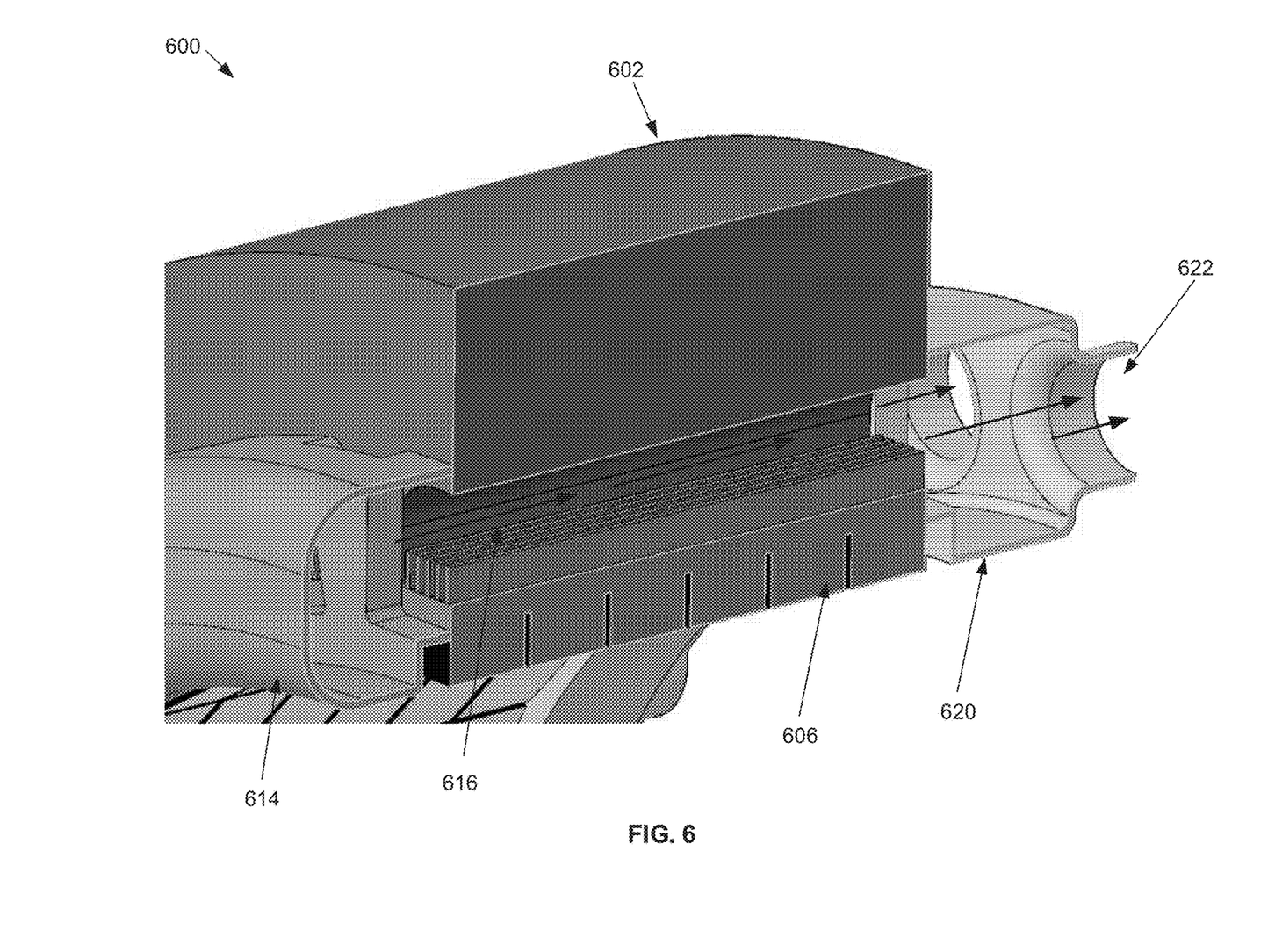
FIG. 6 is a cut-away view of the example air-cooled PET scanner gantry structure with detectors of FIG. 5, in accordance with various embodiments.

FIG. 6 is a cut-away view of the example air-cooled PET scanner gantry structure with detectors of FIG. 5, in accordance with various embodiments. Referring to FIG. 6, there is shown a gantry mechanism 600 where air from the air inlet manifold 614 flows via the conduit 616 over the PET detectors 606 to cool the PET detectors 606. The air may then exit via the air outlets 622 in the air outlet manifold 620. It should be noted that the conduit 616 may be an open area above the PET detectors 606. However, some embodiments may comprise a closed conduit that may be in the form of a pipe that runs at least a part of the distance from the air inlet manifold 614 to the air outlet manifold 620.

Figure 7A:
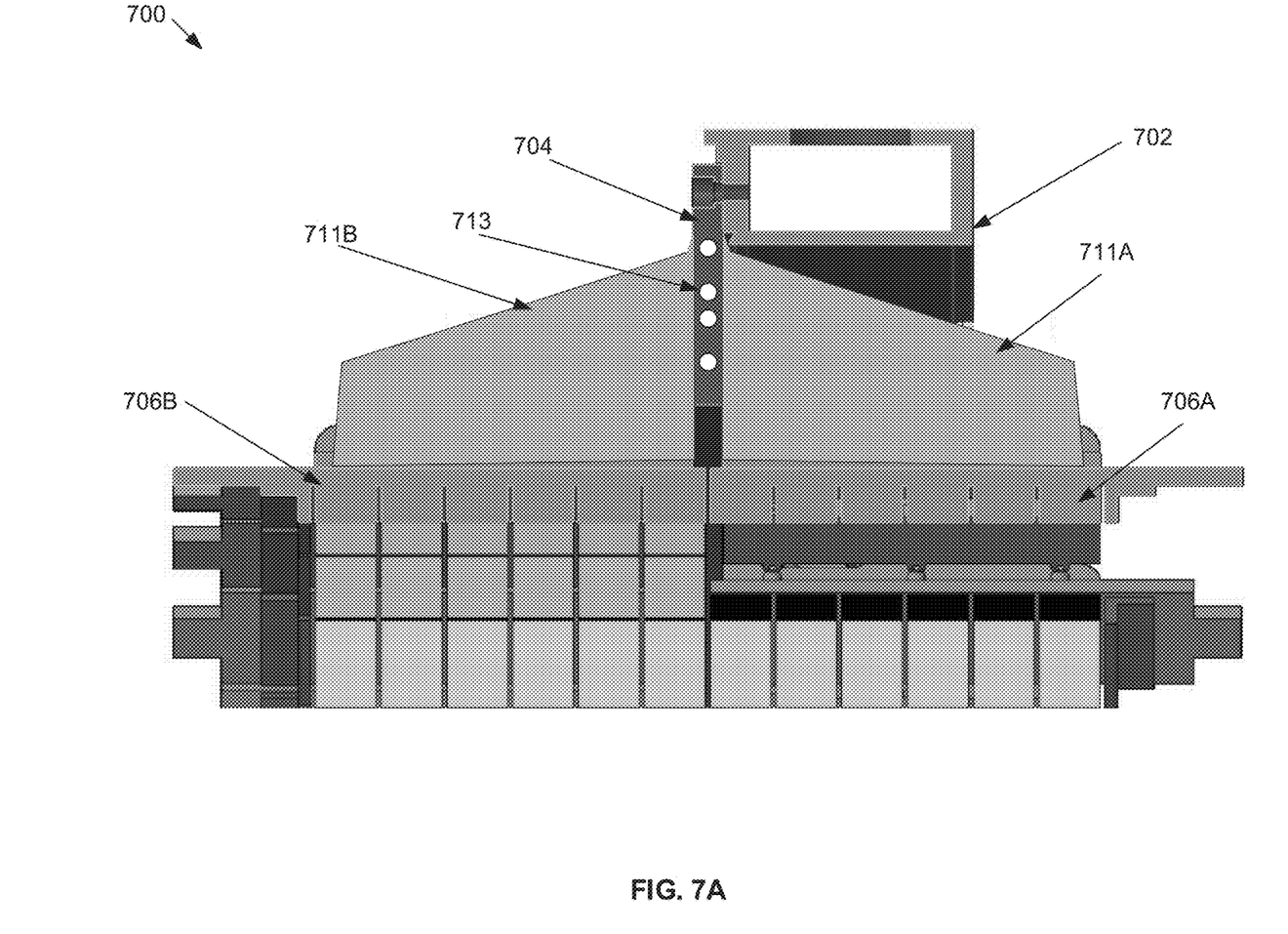
FIG. 7A is a cross-section of a side view of an example liquid-cooled PET scanner gantry structure with detectors, in accordance with various embodiments.

FIG. 7A is a cross-section of a side view of an example liquid-cooled PET scanner gantry structure with detectors, in accordance with various embodiments. Referring to FIG. 7A, there is shown a gantry mechanism 700 comprising a gantry structure 702, PET detectors 706A and 706B, an adaptor plate 704 with cooling liquid coils 713, and holding structures 711A and 711B.

The holding structures 711A and 711B may be coupled to the PET detectors 706A and 706B and to the adaptor plate 704. The coupling may be removable coupling using, for example, mechanical devices such as bolts and/or nuts. The coupling may also be removable coupling using, for example, heat conductive adhesives. In some embodiments, the adhesive may be loosened using a chemical.

The holding structures 711A and 711B may act as heat sinks to transfer heat from the PET detectors 706A and 706B to the adaptor plate 704. Accordingly, the holding structures 706A and 706B may encircle the PET detectors 706A and 706B. The holding structures 706A and 706B may be a solid structure, or may comprise fins for further dissipation of heat from the PET detectors 706A and 706B. The adaptor plate 704 may have cooling liquid coils 713 for removing heat from the adaptor plate 704. The liquid in the cooling liquid coils 713 may be pumped by a pump (not shown).

In some embodiments, the liquid may be pumped into the cooling liquid coils 713, and the discharged liquid exiting the cooling liquid coils 713 may not be reused. In other embodiments, the discharged liquid may be, for example, held in a holding tank (not shown) to be reused at a later time after the liquid has cooled down. In still other embodiments, the liquid may be cooled, for example, as a refrigerant may be cooled for a refrigerator, and then pumped back to the adaptor plate 704. Accordingly, the liquid may be any of many different types of liquids that may be used for cooling. For example, the liquid may be water or some aqueous solution, or an appropriate refrigerant.

While the cross-section view of the adaptor plate 704 shows four conduits, various examples of the disclosure may have more or less conduits shown in a cross-section. Additionally, while the cooling liquid coils 713 are shown as being centered in the adaptor plate 704, various embodiments may have the cooling liquid coils 713 offset to one side or the other. For example, a first coil may be offset to be closer to the holding structures 711A and a second coil may be offset to be closer to the holding structure 711b, etc.

Figure 7B:
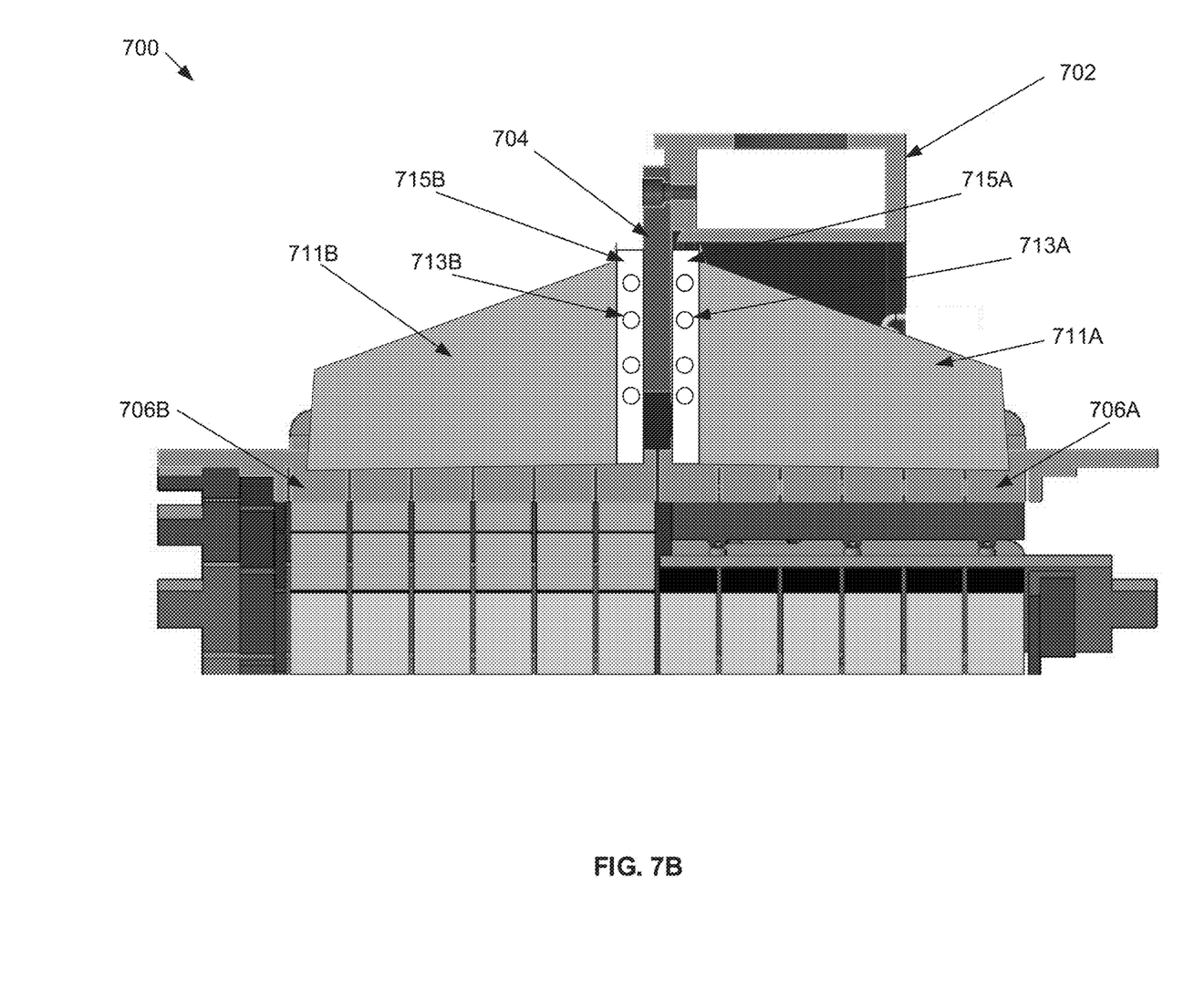
FIG. 7B is a cross-section of a side view of another example liquid-cooled PET scanner gantry structure with detectors, in accordance with various embodiments.

FIG. 7B is a cross-section of a side view of another example liquid-cooled PET scanner gantry structure with detectors, in accordance with various embodiments. Referring to FIG. 7B, there is shown a similar configuration as in FIG. 7A except that the cooling liquid coils 713 of FIG. 7A is shown in external cooling structures 715A and 715B, in which the cooling liquid coils 713A and 713B, respectively, are placed.

It should be noted that for FIGS. 7A and 7B, when there is only one set of PET detectors 706A, there may only be one holding structure 711A, and, in the case of FIG. 7B, only one external cooling structure 715A.

Accordingly, it can be seen that the disclosure provides for an imaging system 100 with an adaptor plate 304 configured to be removably coupled to a gantry structure 302 of the imaging system, a plurality of detectors 306A and 306B configured to be removably coupled to the adaptor plate 304, and one or more conduits 713 or 616 for a fluid to flow through, wherein the fluid is used to cool the imaging system. The fluid may be air (gas) or liquid.

The adaptor plate 304 may be one of several differently sized adaptor plates, where the specific size of the adaptor plate is selected based on the gantry bore size desired. At least two of the differently sized adaptor plates may be configured to be removably attached to a different respective number of detectors. Accordingly, adaptor plates with smaller gantry bore sizes may use fewer detectors, thereby reducing cost of the imaging system.

The detectors may be removably attached to both sides of the adaptor plate. In an embodiment, the imaging system may be configured to allow air to flow through the one or more conduits 616, and the one or more conduits 616 may be configured to carry the air over the plurality of detectors 606 to help cool the detectors. In some embodiments, the air may be cooled prior to being provided to the one or more conduits.

There may be at least one air inlet manifold 614, where the air is provided to the one or more conduits 616 via the at least one air inlet manifold 614. There may also be at least one air outlet manifold 620, where the at least one air outlet manifold 620 may receive the air from at least one of the one or more conduits 616.

In an embodiment, the imaging system 100 may be configured to allow liquid to flow through the one or more conduits, where the conduits 713 may be in the adaptor plate 704. The conduits may form at least one coil 713 in the adaptor plate 704. In another embodiment, the one or more conduits may comprise at least one coil 713A/713B that is external to the adaptor plate 704. There may be, for example, at least one coil 713A/713B on each side of the adaptor plate 704. The liquid may be cooled prior to being provided to the one or more conduits.

It may also be seen that the disclosure provides for an air-cooled imaging system of FIGS. 5 and 6 comprising an adaptor plate 504, which may be one of a plurality of differently sized adaptor plates, configured to be removably coupled to a gantry structure 502 of the imaging system 100, a plurality of detectors 506 configured to be removably coupled to the adaptor plate 504, and one or more conduits 616 for air to flow through, wherein the air is used to cool the imaging system 100. The one or more conduits 616 are configured to carry the air over the plurality of detectors 606. At least two of the differently sized adaptor plates are configured to be removably attached to a different respective number of detectors 606.

Furthermore, the disclosure also provides for a liquid-cooled imaging system of FIGS. 7A and 7B comprising an adaptor plate 704, which may be one of a plurality of differently sized adaptor plates, configured to be removably coupled to a gantry structure 702 of the imaging system 100, a plurality of detectors 706A/706B configured to be removably coupled to the adaptor plate 704, and one or more conduits 713/713A/713B for a liquid to flow through, wherein the liquid is used to cool the imaging system. The one or more conduits comprise one or both of: at least one coil 713A/713B that is external to the adaptor plate 704, and at least one coil 713 in the adaptor plate 704. At least two of the differently sized adaptor plates are configured to be removably attached to a different respective number of detectors 706A/706B.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What are claimed:

1. An imaging system, comprising:
   a gantry structure;
   an adaptor plate selected from a plurality of adaptor plates, each of the plurality of adaptor plates being circular and defining a different bore size through a center of a respective adaptor plate, wherein the adaptor plate is removably coupled to the gantry structure;
   a plurality of detectors removably coupled to the adaptor plate; and
   at least one conduit comprising an inlet configured to receive a fluid and an outlet configured to discharge the fluid carried through the at least one conduit, wherein a first temperature of the fluid received at the inlet is less than a second temperature of the fluid discharged at the outlet.

2. The imaging system of claim 1, wherein a number of the plurality of detectors removably coupled to the adaptor plate is based on the bore size of the adaptor plate.

3. The imaging system of claim 1, wherein at least two of the plurality of adaptor plates are configured to be removably attached to a different respective number of detectors.

4. The imaging system of claim 1, wherein the plurality of detectors are removably attached to both sides of the adaptor plate.

5. The imaging system of claim 1, wherein the fluid is an air flow, and wherein the at least one conduit is configured to carry the air flow over the plurality of detectors.

6. The imaging system of claim 5, comprising a blower configured to cool the air flow and provide the air flow to the inlet of the at least one conduit.

7. The imaging system of claim 5, comprising at least one air inlet manifold configured to provide the air flow to the inlet of the at least one conduit.

8. The imaging system of claim 5, comprising at least one air outlet manifold configured to receive the air flow from the outlet of the at least one conduit.

9. The imaging system of claim 1, wherein the fluid is a liquid, and wherein the at least one conduit is configured to carry the liquid through the at least one conduit.

10. The imaging system of claim 9, wherein the at least one conduit is in the adaptor plate.

11. The imaging system of claim 10, wherein the at least one conduit forms at least one coil in the adaptor plate.

12. The imaging system of claim 9, wherein the at least one conduit comprises at least one coil that is external to the adaptor plate.

13. The imaging system of claim 9, wherein the at least one conduit comprises a first conduit comprising at least one coil adjacent a first side of the adapter plate and a second conduit comprising a second coil adjacent a second side of the adapter plate.

14. The imaging system of claim 9, wherein the liquid is cooled prior to being provided to the one or more conduits.

15. An air-cooled imaging system, comprising:
    a gantry structure;
    an adaptor plate selected from a plurality of adaptor plates, each of the plurality of adaptor plates being circular and defining a different bore size through a center of a respective adaptor plate, wherein the adaptor plate is, removably coupled to the gantry structure;
    a plurality of detectors removably coupled to the adaptor plate;
    at least one conduit comprising an air inlet configured to receive an air flow and an air outlet configured to discharge the air flow carried through the at least one conduit;
    at least one air inlet manifold configured to provide the air flow to the air inlet of the at least one conduit; and
    at least one air outlet manifold configured to receive the air flow from the outlet of the at least one conduit.

16. The air cooled imaging system of claim 15, wherein the at least one conduit carries the air flow over the plurality of detectors.

17. The air cooled imaging system of claim 15, wherein a first temperature of the air flow received at the air inlet is less than a second temperature of the air flow discharged at the air outlet.

18. A liquid-cooled imaging system, comprising:
    a gantry structure;
    an adaptor plate selected from a plurality of adaptor plates, each of the plurality of adaptor plates being circular and defining a different bore size through a center of a respective adaptor plate, wherein the adaptor plate is removably coupled to the gantry structure;
    a plurality of detectors configured to be removably coupled to the adaptor plate; and
    at least one conduit comprising an inlet configured to receive a liquid and an outlet configured to discharge the liquid carried through the at least one conduit, wherein the at least one conduit comprises one or both of:
    at least one coil that is external to the adaptor plate, and
    at least one coil in the adaptor plate.

19. The liquid-cooled imaging system of claim 18, wherein a first temperature of the liquid received at the inlet is less than a second temperature of the liquid discharged at the outlet.

20. The liquid cooled imaging system of claim 18, wherein a number of the plurality of detectors removably coupled to the adaptor plate is based on the bore size of the adaptor plate.

* * * * *